US00PP29695P3

(12) United States Plant Patent
Yamada

(10) Patent No.: US PP29,695 P3
(45) Date of Patent: Sep. 18, 2018

(54) ***CALIBRACHOA* PLANT NAMED 'SUNCAL 1871'**

(50) Latin Name: ***Calibrachoa* sp.**
Varietal Denomination: Suncal 1871

(71) Applicant: Masahiro Yamada, Shiga (JP)

(72) Inventor: Masahiro Yamada, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 66 days.

(21) Appl. No.: 15/530,379

(22) Filed: Jan. 4, 2017

(65) Prior Publication Data

US 2018/0192568 P1 Jul. 5, 2018

(51) Int. Cl.
*A01H 5/02* (2018.01)

(52) U.S. Cl.
USPC ..... Plt./413
CPC ..... *A01H 5/02* (2013.01)

(58) Field of Classification Search
USPC ..... Plt./263.1, 413
See application file for complete search history.

*Primary Examiner* — Susan Beth McCormick Ewoldt
*Assistant Examiner* — Karen M Redden
(74) *Attorney, Agent, or Firm* — C. A. Whealy

(57) ABSTRACT

A new and distinct cultivar of *Calibrachoa* plant named 'Suncal 1871', characterized by its compact and mounding plant habit; vigorous growth habit; freely branching habit; early and freely flowering habit; long flowering period; white-colored flowers with bright yellow-colored throats; and good garden performance.

1 Drawing Sheet

Botanical designation: *Calibrachoa* sp.
Cultivar denomination: 'SUNCAL 1871'.

BACKGROUND OF THE INVENTION

The present invention relates to a new and distinct cultivar of *Calibrachoa* plant, botanically known as *Calibrachoa* sp. and hereinafter referred to by the name 'Suncal 1871'.

The new *Calibrachoa* plant is a product of a planned breeding program conducted by the Inventor in Higashiomi, Shiga, Japan. The objective of the breeding program is to develop new compact, mounding and freely branching *Calibrachoa* plants with numerous large and attractive flowers with unique coloration.

The new *Calibrachoa* plant originated from a cross-pollination conducted by the Inventor in Higashiomi, Shiga, Japan in September, 2012 of a proprietary selection of *Calibrachoa* sp. identified as code number C24F1-81-1, not patented, as the female, or seed, parent with a proprietary selection of *Calibrachoa* sp. identified as code number C24-162-1, not patented, as the male, or pollen, parent. The new *Calibrachoa* plant was discovered and selected by the Inventor as a single flowering plant from within the progeny of the stated cross-pollination in a controlled greenhouse environment in Higashiomi, Shiga, Japan in October, 2013.

Asexual reproduction of the new *Calibrachoa* plant by terminal vegetative cuttings in a controlled greenhouse environment in Higashiomi, Shiga, Japan since November, 2013 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Suncal 1871'. These characteristics in combination distinguish 'Suncal 1871' as a new and distinct *Calibrachoa* plant:

1. Compact and mounding plant habit.
2. Vigorous growth habit.
3. Freely branching habit.
4. Early and freely flowering habit.
5. Long flowering period.
6. White-colored flowers with bright yellow-colored throats and venation.
7. Good garden performance.

Plants of the new *Calibrachoa* can be compared to plants of the female parent selection. Plants of the new *Calibrachoa* differ primarily from plants of the female parent selection in flower color as plants of the female parent selection have red and yellow-colored flowers.

Plants of the new *Calibrachoa* can be compared to plants of the male parent selection. Plants of the new *Calibrachoa* differ primarily from plants of the male parent selection in flower color as plants of the male parent selection have pink and yellow-colored flowers. In addition, flowers of plants of the new *Calibrachoa* are smaller than flowers of plants of the male parent selection.

Plants of the new *Calibrachoa* can also be compared to plants of *Calibrachoa* sp. 'Sunbel 789', disclosed in U.S. Plant Pat. No. 26,444. In side-by-side comparison, plants of the new *Calibrachoa* and 'Sunbel 789' differ primarily in the following characteristics:

1. Plants of the new *Calibrachoa* are larger than plants of 'Sunbel 789'.
2. Plants of the new *Calibrachoa* have thicker lateral branches than plants of 'Sunbel 789'.

3. Plants of the new *Calibrachoa* and 'Sunbel 789' differ in leaf shape as plants of 'Sunbel 789' have spatulate-shaped leaves.
4. Plants of the new *Calibrachoa* have smaller flowers than plants of 'Sunbel 789'.
5. Plants of the new *Calibrachoa* and 'Sunbel 789' differ slightly in flower color.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the top of the sheet comprises a side perspective view of a typical flowering plant of 'Suncal 1871' grown in a container.

The photograph at the bottom of the sheet is a close-up view of a typical flowering plant of 'Suncal 1871'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Calibrachoa* production. During the production of the plants, day temperatures averaged 23° C. and night temperatures averaged 13° C. Plants were three months old when the photographs and the description were taken. In the following description, color references are made to The Royal Horticultural Society Colour Chart, 2007 Edition, except where general terms of ordinary dictionary significance are used.

Botanical classification: *Calibrachoa* sp. 'Suncal 1871'.

Parentage:

*Female, or seed, parent*.—Proprietary selection of *Calibrachoa* sp. identified as code number C24F1-81-1, not patented.

*Male, or pollen, parent*.—Proprietary selection of *Calibrachoa* sp. identified as code number C24-162-1, not patented.

Propagation:

*Type*.—By vegetative terminal cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous; white in color.

*Rooting habit*.—Freely branching.

Plant description:

*Plant and growth habit*.—Compact and mounding plant habit; freely branching habit with numerous lateral branches developing per plant; pinching enhances lateral branch development; vigorous growth habit.

*Plant height*.—About 25 cm.

*Plant diameter*.—About 57 cm.

Lateral branch description:

*Length*.—About 24 cm.

*Diameter*.—About 3.6 mm.

*Internode length*.—About 2.5 cm.

*Strength*.—Strong.

*Aspect*.—Upright to outwardly.

*Texture*.—Densely pubescent; rough.

*Color*.—Close to 144B.

Leaf description:

*Arrangement*.—Alternate, simple.

*Length*.—About 3.5 cm.

*Width*.—About 1.65 cm.

*Shape*.—Elliptic.

*Apex*.—Obtuse.

*Base*.—Attenuate.

*Margin*.—Entire.

*Texture, upper and lower surfaces*.—Pubescent; rough.

*Venation pattern*.—Pinnate; reticulate.

*Color*.—Developing leaves, upper surface: Close to 137B. Developing leaves, lower surface: Close to 138A. Fully expanded leaves, upper surface: Close to N137B; venation, close to 144B. Fully expanded leaves, lower surface: Close to 147B; venation, close to 144C.

*Petioles*.—Length: About 4.4 mm. Diameter: About 2.1 mm. Texture, upper and lower surfaces: Pubescent; rough. Color, upper and lower surfaces: Close to 145B.

Flower description:

*Flower arrangement and habit*.—Single salverform flowers arising from upper leaf axils; freely flowering habit with usually about 140 flowers developing per plant; flowers face upright or upright to outwardly.

*Fragrance*.—None detected.

*Natural flowering season*.—Early flowering habit, plants of the new *Calibrachoa* initiate and develop flowers about three to four weeks after planting; long flowering period, flowering naturally commences during the spring and plants flower continuously throughout the summer until late autumn in Japan.

*Flower longevity*.—Individual flowers last about seven to ten days on the plant; flowers not persistent.

*Flower diameter*.—About 3.3 cm.

*Flower length (depth)*.—About 8.8 mm.

*Throat diameter*.—About 6.5 mm.

*Tube length*.—About 1.5 cm.

*Tube diameter, base*.—About 1.4 mm.

*Flower buds*.—Length: About 1.9 cm. Diameter: About 1 cm. Shape: Cylindrical. Color: Close to 5D and 2C; proximally, close to 150C.

*Corolla*.—Arrangement: Five petals fused at the base and opening into a flared trumpet. Petal length from throat: About 9.7 mm. Petal width: About 1.2 cm. Petal shape: Roughly spatulate. Petal apex: Rounded. Petal margin: Entire; undulate. Petal texture, upper surface: Smooth, glabrous; satiny. Petal texture, lower surface: Smooth, glabrous. Throat texture: Smooth, glabrous. Tube texture: Pubescent. Color: Petal, when opening, upper surface: Close to 4D; towards the throat, close to 7A. Petal, when opening, lower surface: Close to 155B. Petal, fully opened, upper surface: Close to 155B; towards the throat, close to 7B; venation, close to 3B. Petal, fully opened, lower surface: Close to NN155A. Throat: Close to 13A; proximally, close to 2C; venation, close to N144A. Tube: Close to 13C; proximally, close to 1C.

*Calyx*.—Arrangement: Star-shaped tubular calyx tube with five sepals in a single whorl and fused at the base. Sepal length: About 8.1 mm. Sepal width: About 2.8 mm. Sepal shape: Lanceolate. Sepal apex: Acute. Sepal margin: Entire. Sepal texture, upper and lower surfaces: Pubescent; rough. Sepal color: Immature and mature, upper surface: Close to N137D. Immature and mature, lower surface: Close to 137B.

*Peduncles*.—Length: About 1.1 cm. Diameter: About 0.5 mm. Angle: Upright to outwardly. Strength: Strong. Texture: Pubescent; rough. Color: Close to 144B.

*Reproductive organs*.—Stamens: Quantity: Five per flower. Filament length: About 8.7 mm. Filament color: Close to 145C. Anther shape: Ellipsoidal. Anther size: About 1.5 mm by 1 mm. Anther color: Close to 4C. Pollen amount: Scarce. Pollen color: Close to 4D. Pistils: Quantity: One per flower. Pistil length: About 9.8 mm. Style color: Close to 145D. Stigma shape: Transversely ellipsoidal. Stigma color: Close to 145B. Ovary color: Close to 144A.

*Seeds and fruits*.—Seed and fruit development have not been observed on plants of the new *Calibrachoa*.

Garden performance: Plants of the new *Calibrachoa* have been observed to have good garden performance and to tolerate wind, rain and temperatures ranging from about 5° C. to about 35° C.

Pathogen & pest resistance: Plants of the new *Calibrachoa* have not been observed to be resistant to pests and pathogens common to *Calibrachoa* plants.

It is claimed:

1. A new and distinct *Calibrachoa* plant named 'Suncal 1871' as illustrated and described.

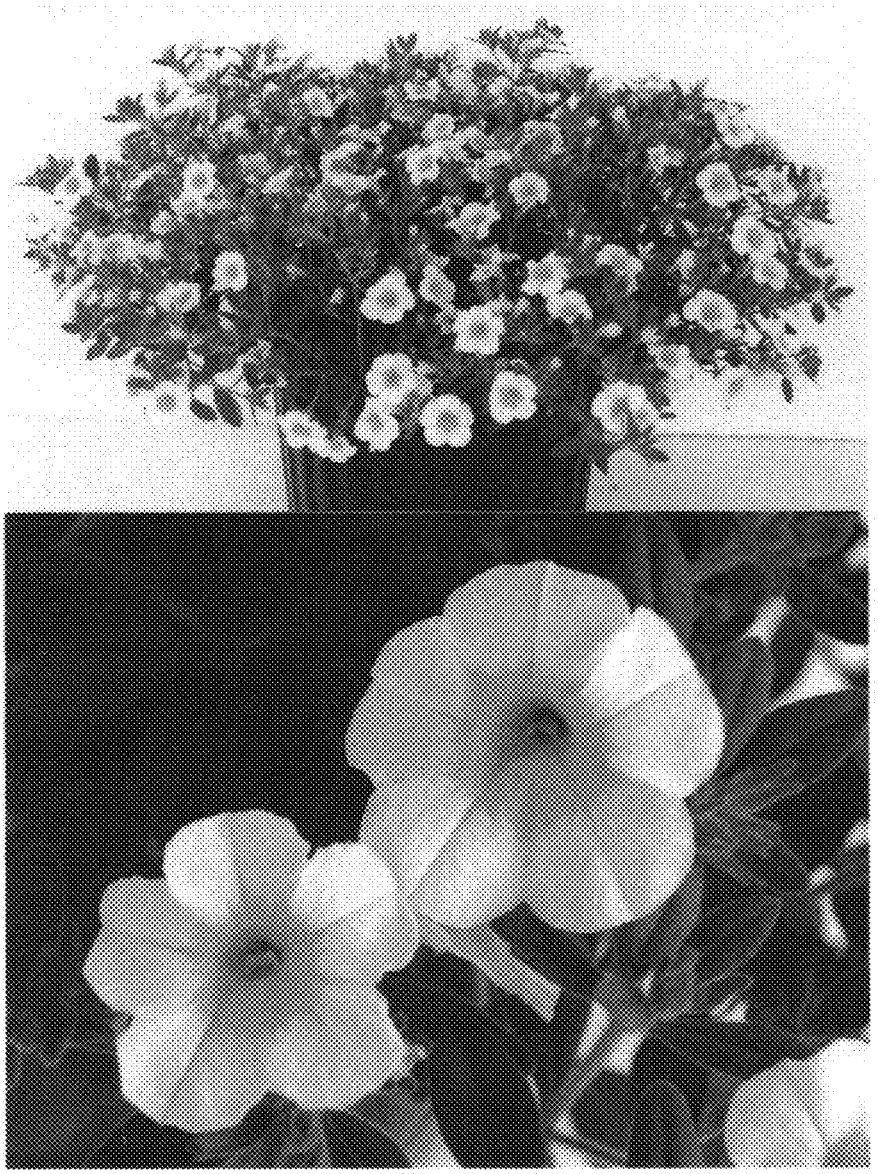

* * * * *